United States Patent
Myrick et al.

(10) Patent No.: US 12,194,420 B2
(45) Date of Patent: *Jan. 14, 2025

(54) METHOD FOR BUBBLE-FREE GAS-ENRICHMENT OF A FLOWING LIQUID WITHIN A CONDUIT

(71) Applicant: TherOx, Inc., Irvine, CA (US)

(72) Inventors: Stephen E. Myrick, Tustin, CA (US); Jeffrey L. Creech, Los Angeles, CA (US)

(73) Assignee: TherOx, Inc., Irvine, CA (US)

( * ) Notice: Subject to any disclaimer, the term of this patent is extended or adjusted under 35 U.S.C. 154(b) by 264 days.

This patent is subject to a terminal disclaimer.

(21) Appl. No.: 17/860,514

(22) Filed: Jul. 8, 2022

(65) Prior Publication Data

US 2023/0022647 A1    Jan. 26, 2023

Related U.S. Application Data

(60) Continuation of application No. 17/189,054, filed on Mar. 1, 2021, now Pat. No. 11,420,165, which is a
(Continued)

(51) Int. Cl.
  *B01F 23/232* (2022.01)
  *A61M 1/16* (2006.01)
  (Continued)

(52) U.S. Cl.
  CPC .......... *B01F 23/232* (2022.01); *A61M 1/32* (2013.01); *B01F 23/23413* (2022.01);
  (Continued)

(58) Field of Classification Search
  CPC .. B01F 23/232; B01F 25/23; B01F 25/31331; B01F 23/454; B01F 33/821;
  (Continued)

(56) References Cited

U.S. PATENT DOCUMENTS

| | | |
|---|---|---|
| 2,901,112 A | 8/1959 | Henry |
| 3,862,715 A | 1/1975 | Remenyik |

(Continued)

FOREIGN PATENT DOCUMENTS

| | | |
|---|---|---|
| DE | 271787 | 9/1912 |
| EP | 0692273 | 1/1996 |

*Primary Examiner* — Lauren P Farrar
(74) *Attorney, Agent, or Firm* — Fish & Richardson P.C.

(57) ABSTRACT

The present invention provides a system for enriching a flowing liquid with a dissolved gas inside a conduit. The system comprises two or more capillaries, each capillary delivering a stream of a gas-enriched liquid to the flowing liquid. The first ends of the capillaries are positioned to form an intersecting angle with respect to the effluent streams such that these streams of gas-enriched liquid collide with each other upon exit from the first ends of the capillaries, effecting localized convective mixing within the larger liquid conduit before these gas-enriched streams are able to come into close contact with the boundary surfaces of the conduit, whereby the gas-enriched liquid mixes with the flowing liquid to form a gas-enriched flowing liquid. In the preferred embodiment, no observable bubbles are formed in the gas-enriched flowing liquid. Methods of making and using such system are also provided.

17 Claims, 7 Drawing Sheets

Related U.S. Application Data continuation of application No. 15/732,975, filed on Jan. 22, 2018, now Pat. No. 10,960,364, which is a division of application No. 13/986,361, filed on Apr. 23, 2013, now Pat. No. 9,919,276.

(60) Provisional application No. 61/687,781, filed on May 1, 2012.

(51) Int. Cl.
*A61M 1/32* (2006.01)
*A61M 25/00* (2006.01)
*B01F 23/234* (2022.01)
*B01F 23/454* (2022.01)
*B01F 25/23* (2022.01)
*B01F 25/313* (2022.01)
*B01F 33/82* (2022.01)
*B29C 53/08* (2006.01)

(52) U.S. Cl.
CPC ............ *B01F 23/454* (2022.01); *B01F 25/23* (2022.01); *B01F 25/31331* (2022.01); *B01F 33/821* (2022.01); *A61M 1/1678* (2013.01); *A61M 25/001* (2013.01); *A61M 2202/0476* (2013.01); *B29C 53/083* (2013.01); *B29C 2793/009* (2013.01); *Y10T 29/49826* (2015.01)

(58) Field of Classification Search
CPC .. B01F 23/23413; A62M 1/32; A62M 1/1678; A62M 25/001; A62M 2202/0476; Y10T 29/49826; B29C 53/083; B29C 2793/009
See application file for complete search history.

(56) References Cited

U.S. PATENT DOCUMENTS

| | | |
|---|---|---|
| 3,963,503 A | 6/1976 | Mackenzie |
| 4,041,180 A | 8/1977 | Wilson |
| 4,445,886 A | 5/1984 | Osterholm |
| 4,450,841 A | 5/1984 | Osterholm |
| 4,664,680 A | 5/1987 | Weber |
| 4,808,378 A | 2/1989 | Nakanishi |
| 4,865,836 A | 9/1989 | Long |
| 4,874,509 A | 10/1989 | Bullock |
| 4,927,623 A | 5/1990 | Long |
| 4,963,130 A | 10/1990 | Osterholm |
| 4,965,022 A | 10/1990 | Litz |
| 4,973,558 A | 11/1990 | Wilson et al. |
| 5,029,579 A | 7/1991 | Trammell |
| 5,072,739 A | 12/1991 | John |
| 5,080,885 A | 1/1992 | Long |
| 5,084,011 A | 1/1992 | Grady |
| 5,086,620 A | 2/1992 | Spears |
| 5,108,662 A | 4/1992 | Litz |
| 5,261,875 A | 11/1993 | Spears |
| 5,324,436 A | 6/1994 | John |
| 5,344,393 A | 9/1994 | Roth |
| 5,393,513 A | 2/1995 | Long |
| 5,407,426 A | 4/1995 | Spears |
| 5,527,962 A | 6/1996 | Pavia |
| 5,562,608 A | 10/1996 | Sekins |
| 5,569,180 A | 10/1996 | Spears |
| 5,591,328 A | 1/1997 | Bodnaras |
| 5,599,296 A | 2/1997 | Spears |
| 5,693,017 A | 12/1997 | Spears |
| 5,735,934 A | 4/1998 | Spears |
| 5,797,874 A | 8/1998 | Spears |
| 6,030,357 A | 2/2000 | Daoud |
| 6,180,059 B1 | 1/2001 | Divino |
| 6,213,976 B1 * | 4/2001 | Trerotola ............ A61M 25/104 604/104 |
| 6,241,802 B1 | 6/2001 | Spears |
| 6,248,087 B1 | 6/2001 | Spears |
| RE37,379 E | 9/2001 | Spears |
| 6,312,647 B1 | 11/2001 | Spears |
| 6,315,942 B1 | 11/2001 | Spears |
| 6,344,489 B1 | 2/2002 | Spears |
| 6,387,324 B1 | 5/2002 | Patterson |
| 6,454,997 B1 | 9/2002 | Divino |
| 6,555,059 B1 | 4/2003 | Myrick |
| 6,565,807 B1 | 5/2003 | Patterson |
| 6,576,191 B1 | 6/2003 | Myrick |
| 6,582,387 B2 | 6/2003 | Derek |
| 6,596,235 B2 | 7/2003 | Divino |
| 6,602,467 B1 | 8/2003 | Divino |
| 6,602,468 B2 | 8/2003 | Patterson |
| 6,607,698 B1 | 8/2003 | Spears |
| 6,613,280 B2 | 9/2003 | Myrick |
| 6,622,542 B2 | 9/2003 | Daw |
| 6,676,900 B1 * | 1/2004 | Divino, Jr. .......... A61M 1/3603 604/4.01 |
| 6,746,417 B2 | 6/2004 | Spears |
| 6,759,008 B1 | 7/2004 | Patterson |
| 6,811,750 B2 | 11/2004 | Patterson |
| 6,843,099 B2 | 1/2005 | Daw |
| 6,849,235 B2 | 2/2005 | Myrick |
| 6,855,291 B2 | 2/2005 | Patterson |
| 6,890,482 B2 | 5/2005 | Divino |
| 6,899,847 B2 | 5/2005 | Myrick |
| 6,936,221 B1 | 8/2005 | Divino |
| 6,974,435 B2 | 12/2005 | Daw |
| 7,013,703 B2 | 3/2006 | Daw |
| 7,172,727 B2 | 2/2007 | Patterson |
| 7,820,102 B2 | 10/2010 | Myrick |
| 8,192,384 B2 | 6/2012 | Myrick |
| 8,246,564 B2 | 8/2012 | Myrick |
| 9,919,276 B2 | 3/2018 | Myrick |
| 10,960,364 B2 | 3/2021 | Myrick |
| 2010/0143190 A1 | 6/2010 | Myrick |
| 2010/0143192 A1 | 6/2010 | Myrick |
| 2010/0145249 A1 | 6/2010 | Myrick |

* cited by examiner

METHOD FOR BUBBLE-FREE GAS-ENRICHMENT OF A FLOWING LIQUID WITHIN A CONDUIT

RELATED APPLICATIONS

This application is a continuation of U.S. patent application Ser. No. 17/189,054, filed on Mar. 1, 2021, which is a continuation of U.S. patent application Ser. No. 15/732,975, filed on Jan. 22, 2018, which is a divisional of U.S. patent application Ser. No. 13/986,361, filed on Apr. 23, 2013, which claims the benefit of U.S. Provisional Application No. 61/687,781, filed May 1, 2012.

BACKGROUND OF THE INVENTION

Area of the Art

The invention relates generally to the system and methods for mixing one liquid with dissolved gas into a second liquid in a bubble free manner to achieve gas enrichment in the second liquid and, more particularly, to the gas enrichment of a flowing liquid within a conduit.

Description of the Prior Art

Gas-enriched liquids are desirable in a wide variety of applications. However, at ambient pressure, the relatively low solubility of many gases, such as oxygen or nitrogen, within a liquid, such as water, produces a relatively low concentration of the dissolved gas in the liquid. One method of obtaining an increase in the gas concentration level without significant increase in liquid volume involves an injection and mixing of a gas-enriched liquid, such as a gas-supersaturated liquid, into a liquid flow path of interest. A liquid can be gas enriched at high pressure through various methods. However, when the gas-supersaturated liquid is delivered to the mixing site at ambient pressures, it has a propensity to form gas bubbles. Thus there is a need for a system and methods for mixing a highly gas enriched liquid into another liquid in a bubble free manner.

Oxygen-enriched liquids are desirable in a variety of medical applications. However, injection of the gas-supersaturated liquid directly into blood within a blood vessel without adequate mixing of the gas-supersaturated liquid and the blood may lead to localized pockets of the liquid having high levels of gas supersaturation. The presence of these pockets of the gas-supersaturated liquid within blood vessels may lead to nucleation of oxygen bubbles from the gas-supersaturated liquid with accompanying entrainment of undesirable bubbles in the blood stream. Gas bubbles may occlude the blood vessels and result in a gaseous local embolism that causes a decrease in local circulation, arterial hypoxemia, and systemic hypoxia. The inhibition of gaseous emboli formation is highly desirable for this application.

To solve this problem of gaseous emboli formation, conventional methods for the delivery of oxygenated blood or oxygen-enriched liquids to tissues and bodily liquids involve the use of extracorporeal circuits for blood oxygenation. Extracorporeal circuits require withdrawing blood from a patient, circulating the blood through an oxygenator to increase blood oxygen concentration, and then delivering the blood back to the patient. There are drawbacks, however, to the use of conventional oxygenators in an extracorporeal circuit. In general, they are not operated and monitored automatically, and the presence of a qualified perfusionist is typically required. Accordingly, such systems typically are costly, complex, and difficult to operate.

Conventional extracorporeal circuits also exhibit other drawbacks. For example, extracorporeal circuits typically have a relatively large priming volume. The priming volume is typically the volume of blood contained within the extracorporeal circuit, i.e., the total volume of blood that is outside of the patient's body at any given time. For example, it is not uncommon for the extracorporeal circuit to hold one to two liters of blood for a typical adult patient. Such large priming volumes are undesirable for many reasons. For example, in some cases a blood transfusion may be necessary to compensate for the blood temporarily lost to the extracorporeal circuit because of its large priming volume. Also, a heat exchanger must be used to maintain the temperature of the blood at an acceptable level as it travels through the extracorporeal circuit. Further, conventional extracorporeal circuits are relatively difficult to turn on and off. For instance, if the extracorporeal circuit is turned off, large stagnant pools of blood in the circuit might coagulate.

In addition to the drawbacks mentioned above, in extracorporeal circuits that include conventional blood oxygenators, there is a relatively high risk of inflammatory cell reaction and blood coagulation due to the relatively large blood contact surface area of the oxygenators. Conventional membrane-type blood oxygenators are gas-liquid contact devices, and require efficient surface contact between gas and blood. The exposure of blood to both solid surface and gas contact triggers a host of inflammatory processes, begins the process of protein denaturation, and acts to promote the coagulation cascade. For example, a blood contact surface area of about one to two square meters are not uncommon with conventional oxygenator systems. Thus, relatively aggressive anti-coagulation therapy, such as heparinization, is usually required as an adjunct to using the oxygenator. Anti-coagulation therapy increases the risk of bleeding.

An additional limitation of conventional gas-liquid membrane-based blood oxygenators is the maximum gas-enrichment that may be imparted to the blood; the gas concentration in the blood is expressed typically as an oxygen partial pressure, or pO2 level. Under optimal conditions, conventional blood oxygenation systems can elevate the arterial blood $pO_2$ to a maximum level of approximately 500 mmHg. Thus, if the benefits of hyperbaric medicine are to be realized, i.e. with blood having $pO_2$ levels at or above one atmosphere, or 760 mmHg, this result cannot be achieved with conventional oxygenators.

A new technology for producing hyperbaric blood pO2 levels has been developed as described in U.S. Pat. No. 6,387,324. This technology, referred to as Supersaturated Oxygen Therapy ($SSO_2$ Therapy), develops higher oxygen concentrations than conventional means, but still requires that the fluid to be oxygenated be pumped to an oxygenation device to mix with a highly oxygen-enriched fluid, then be returned as an oxygenated fluid. In the case of oxygenating patient blood, this is defined as an extracorporeal circuit.

SUMMARY OF THE INVENTION

In view of these disadvantages of the conventional devices and methods for enriching liquids with high concentrations of dissolved gas, it is an object of the present invention to provide devices and methods for enriching a liquid within a conduit with a dissolved gas without use of external mixing circuits and in a manner which prevents or minimizes bubble formation.

This and other objects and advantages are achieved in the system of the present invention for enriching a flowing liquid inside a conduit with a dissolved gas. The system comprises two or more capillaries, each capillary delivering a stream of a gas-enriched liquid into the flowing liquid contained in the conduit. The first end (outlet) of each capillary is positioned inside the conduit in fluid communication with the flowing liquid. The first ends of the capillaries form an intersecting angle with respect to the effluent stream of other capillary such that these streams of gas-enriched liquid collide with each other upon exit from the first ends of the capillaries, effecting localized convective mixing within the larger liquid conduit before these gas-enriched streams are able to come into close contact with the boundary surfaces of the conduit. This localized convective mixing that is achieved by the geometric apposition of the streams acts to rapidly achieve a nearly homogeneous concentration (mixing cup concentration) in the surrounding liquid without exposing the localized 'hot spots' of high gas concentration to potential bubble nucleation from the boundary surfaces. In one embodiment, the capillaries are contained within a tip of a catheter adapted for positioning within the enclosed area in communication with the bodily liquid. The second ends of the capillaries are connected to a single tube within the catheter to be supplied with a source of gas-enriched fluid.

The gas-enriched liquid introduced through the capillaries may be water, physiologic solution, or biocompatible liquid-liquid emulsions; these gas-enriched liquids may advantageously contain ancillary therapeutic agents that are desirable to be delivered in combination with the gas-enriched liquid. In the case of liquid-liquid emulsions, a dispersed non-aqueous phase may be incorporated stably into the solution by conventional means in order to enhance gas solubility or incorporate water-immiscible therapeutic agents (such as perfluorocarbons or crystalloids). The bodily liquid may be blood, cerebrospinal fluid, or interstitial liquid. The gas may be oxygen, ozone, nitrogen, air, an inert gas, or a non-inert gas that is desired to add directly to the bodily liquid for therapeutic effect. The conduit may be an enclosed area such as a blood vessel.

The second ends of the capillaries (catheter inlet) may be operatively coupled to a cartridge, the source for the gas-enriched liquid. In one embodiment, the cartridge comprises a housing and an enrichment device disposed in the housing to form a gas-enriched liquid. The enrichment device may comprise an atomizing chamber adapted to receive the gas through a gas inlet and an atomizer disposed within the atomizing chamber. The atomizing chamber is pressurized with the gas that is to be dissolved into the liquid. The atomizer is adapted to receive a liquid from a fluid supply assembly (piston pump) and to atomize the liquid upon delivery into the atomizing chamber, exposing the liquid to the pressurized gas and dissolving the gas efficiently to form the gas-enriched liquid.

In another aspect, the present invention provides a method of operating a system for enriching a liquid with a dissolved gas inside a conduit. The method comprises: (a) providing two or more capillaries each having first and second ends for delivery of a gas-enriched liquid; (b) the first ends form an intersecting angle with respect to the effluent streams such that these streams of gas-enriched liquid collide with each other upon exit from the first ends of the capillaries, effecting localized convective mixing within the larger liquid conduit before these gas-enriched streams are able to come into close contact with the boundary surfaces of the conduit; and (c) operatively connecting the second ends of the capillaries to a source of the gas-enriched liquid.

In one embodiment, the step (a) further comprises: (a1) providing a single lumen polymer capillary tube; (a2) wrapping the tube around a curved tool with a known radius to form a capillary of a modified shape having a curved segment; and (a3) cutting and removing a part of the curved segment to form two capillaries with exposed lumen. Preferably, the cutting step (a3) is conducted in such a way that each of the obtained two capillaries has a curved portion, wherein the end of the curved portion is the first end of the capillary.

In another embodiment, the step (a) further comprises: (a1) providing a separate capillary tube for each capillary end; (a2) inserting each tube into a slot on a tip adapter in such a way as to produce the geometry for intersecting capillary jets; and (a3) holding each capillary in place with an outer sleeve that could be shrunk over the tip to lock the capillaries in place.

In another aspect, the present invention provides a method of enriching a liquid with a dissolved gas inside a conduit. The method comprises: (a) providing two or more capillaries for delivery of a gas-enriched liquid, each capillary having first and second ends, wherein the first ends form an intersecting angle with respect to the effluent streams such that these streams of gas-enriched liquid collide with each other upon exit from the first ends of the capillaries, effecting localized convective mixing within the larger liquid conduit before these gas-enriched streams are able to come into close contact with the boundary surfaces of the conduit; and (b) delivering the gas-enriched liquid through the capillaries and mixing it with a bodily liquid to form a gas-enriched bodily liquid.

Preferably, the mixing occurs without accompanying bubble formation. For example in one embodiment, evaluation of oxygen-enriched liquid mixing was performed, using a peristaltic pump in combination with a glass tube. Solutions of glycerin and water, and polyacrylamide and water were used in different concentrations to simulate a range of potential bodily liquid viscosities and viscoelastic behavior. In this experiment, the simulated bodily liquid solution was pumped at a fixed flow rate of 110 ml/min through the test circuit, while injecting 4.0 ml/min of oxygen-enriched liquid (with added dye for visual contrast enhancement) through the first ends of the dual capillaries, using a custom in vitro test system. The exit jets streams of the oxygen-enriched liquid were positioned at opposing 45° angles (90° included angle) to effect jet collision just distal to the exit ports of the first ends. The exit region and jet streams were observed and videotaped. When a 40% (v/v) glycerin and water simulated bodily liquid solution was used, video results showed that the colliding exit jet streams of oxygen-enriched liquid quickly dispersed, filling the glass tube (conduit). No evidence of nucleation on the distal outer surface of the capillaries, or in the mixed flow stream, was observed during the test.

The system and methods of the present invention have been found to provide an adequate mixing without production of significant bubbles within a blood vessel of a patient. In the present invention, the gas-enriched liquid may be created in the same manner as previously described in U.S. Pat. No. 6,613,280, entitled "System for Enriching a Bodily Fluid with a Gas," which is incorporated herein by the reference. However, the present invention greatly simplifies the cartridge described in that Patent by entirely eliminating the necessity for extracorporeal mixing of the bodily liquid with the highly gas-enriched liquid. In effect, the present invention improves upon the previously disclosed ex vivo liquid-liquid oxygenation method and apparatus by creating an effective in vivo liquid-liquid oxygenation method and apparatus. Accordingly, the hardware component of the present invention is greatly simplified since many of the features described in U.S. Pat. No. 6,613,280 are not needed, including the blood pump, blood draw tubing, and extracorporeal blood circuit controls.

DESCRIPTION OF THE FIGURES

The aforementioned and other features of this invention and the manner of obtaining them will become more apparent, and will be best understood by reference to the following description, taken in conjunction with the accompanying drawings. These drawings depict only a typical embodiment of the invention and do not therefore limit its scope. They serve to add specificity and detail.

DETAILED DESCRIPTION OF THE PREFERRED EMBODIMENTS

Figure 1:
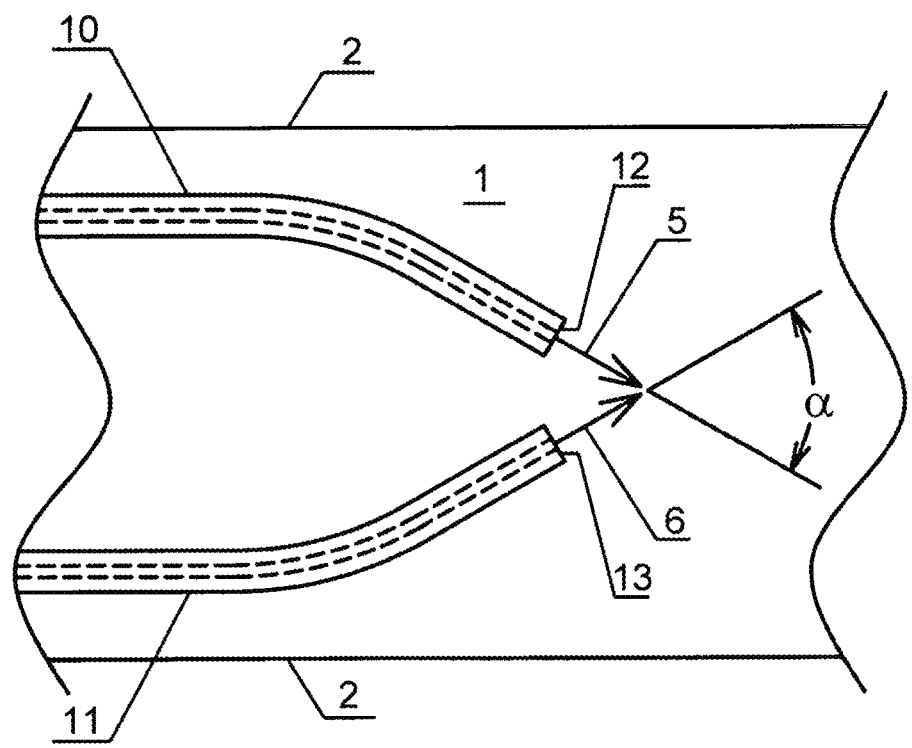
FIG. 1 shows the system of the present invention comprising two capillaries positioned inside an enclosed area of a body in accordance with one embodiment of the present invention.

The present invention provides a system for enriching a bodily liquid with a dissolved gas inside an enclosed area 1 of a body. As shown in FIG. 1, the system comprises two capillaries 10 and 11, each capillary delivering respectively a stream 5 and 6 of a gas-enriched liquid to the bodily liquid. First ends 12 and 13 of the capillaries are positioned inside the enclosed area 1 in a fluid communication with the bodily liquid and form an intersecting angle α with respect to the effluent streams such that these streams of gas-enriched liquid collide with each other upon exit from the first ends of the capillaries, effecting localized convective mixing within the larger liquid conduit before these gas-enriched streams are able to come into close contact with the boundary surfaces 2 of the conduit surrounding the enclosed area 1, whereby the gas-enriched liquid mixes with the bodily liquid to form a gas-enriched bodily liquid.

Henry's Law describes the effect of pressure on the solubility of a gas in a liquid. The law states that the gas solubility at a fixed temperature is proportional to the partial pressure of the gas in phase equilibrium with the liquid. The simple equation for Henry's Law is $p_A = H x_A$, where $p_A$ represents the partial pressure of gas A, H is the Henry's Law constant for gas A in the specified liquid, and $x_A$ is the mole fraction of gas A dissolved in the liquid. For example, at sea level total atmospheric pressure is 760 mmHg and approximately 20.8 percent of this air is oxygen gas. Using the ideal gas law, the partial pressure of oxygen at sea level is 158 mmHg (760 mmHg×0.208=158.08 mmHg). The Henry's Law constant for oxygen solubility in water at 25° C.=$4.55 \times 10^4$ atmosphere/mole fraction $O_2$, or $3.45 \times 10^7$ mmHg/mole fraction $O_2$, the details of which are described in A. X. Schmidt and H. L. List, *Material and Energy Balances*, Prentice-Hall, Englewood Cliffs, N J, 1962. Thus, the mole fraction of oxygen dissolved in water that is exposed to air at standard temperature and pressure (STP) $x_{O2} = pO_2/H = 158/(3.45 \times 10^7) = 4.57 \times 10^{-6}$.

Liquids may be enriched with gas to obtain gas-enriched liquids containing concentrations of the gas that exceed its solubility at ambient pressure; this condition is necessary to have a gas-supersaturated liquid. For example, compression of a gas/liquid mixture at a high pressure may be used to achieve a high dissolved gas concentration. As per Henry's Law, the application of higher pressure will increase the partial pressure of the gas, and the solubility will increase proportionally. E.g., a gas-enriched liquid that has a greater dissolved oxygen concentration than 4.57×10-6 mole fraction in ambient conditions at STP must also have a higher equivalent partial pressure of oxygen than the ambient air level of about 158 mmHg. Such a liquid, for the purposes of the present invention, is defined as a "gas-enriched liquid", meaning a liquid having a gaseous solute concentration that exceeds its equilibrium solubility limit in accordance with Henry's Law.

The gas-enriched liquid of the present application may contain one or more dissolved gases such as oxygen, ozone, an inert gas (for example, helium), nitrogen, nitrous oxide, carbon dioxide and air. In one embodiment, gas-enriched liquid is oxygen-supersaturated liquid that contains a dissolved oxygen concentration (expressed in units of STP gas volume per volume solvent) between 0.5 and 3 ml $O_2$/ml solvent; expressed in terms of $x_{O2}$, this range is $3.68 \times 10^{-4}$ to $2.2 \times 10^{-3}$. For this specific example, the solvent is aqueous in nature. Compared to the amount of oxygen contained in water under ambient conditions, the upper end of this achievable concentration range is $(2.2 \times 10^{-3})/(4.57 \times 10^{-6}) = 483$ times this level.

The oxygen-supersaturated liquid may be supplied to the capillaries at supply pressures from 100 to 10,000 psig, at any supersaturated concentration produced when saturating the fluid at the chosen supply pressure. The supply pressure (operating pressure) is controlled, and the total flow rate will vary depending upon the capillary diameter and length, number of capillaries, and liquid viscosity.

For physiologic applications, oxygen levels typically are described in terms of equivalent partial pressure of oxygen that is in equilibrium with the dissolved gas. Thus, measurements of oxygen concentration in the blood are reported as 'pO2' levels, in units of mmHg, even though the reported quantity is the dissolved gas concentration. For human arterial blood, normal oxygen levels, i.e., normoxia or (less commonly) normoxemia, range from 90 to 160 mmHg. Hypoxic blood, i.e., hypoxia or (less commonly) hypoxemia, is arterial blood with a $pO_2$ less than 90 mmHg. Hyperoxemic blood, i.e., hyperoxia or hyperoxemia, is arterial blood with a $pO_2$ greater than 160 mmHg. As used herein, hyperbaric blood is arterial blood with a $pO_2$ greater than 160 mmHg, or the oxygen concentration of air at standard conditions. In one embodiment, the obtained gas-enriched bodily liquid is blood containing a hyperbaric concentration of oxygen.

For the purposes of the present invention, any gas-enriching device may be used to provide a gas-enriched liquid to the capillaries. For example, gas-enriched liquid may be prepared using apparatus and methods for preparing oxygen-supersaturated liquids disclosed in U.S. Pat. No. 5,407,426 to Spears entitled "Method and Apparatus for Delivering Oxygen into Blood"; U.S. Pat. No. 5,569,180 to Spears entitled "Method for Delivering a Gas-Supersaturated Fluid to a Gas-Depleted Site and Use Thereof"; U.S. Pat. No. 5,599,296 to Spears entitled "Apparatus and Method of Delivery of Gas-Supersaturated Liquids;" U.S. Pat. No. 5,797,874 to Spears entitled "Method of Delivery of Gas-Supersaturated Liquids;" U.S. Pat. No. 6,387,324 to Patterson entitled "Apparatus and Method for Blood Oxygenation", and U.S. Pat. No. 6,613,280 to Myrick, entitled "System for Enriching a Bodily Fluid with a Gas," each of which is incorporated herein in its entirety by reference.

The gas-enriched liquid introduced through the capillaries may be water, physiologic solution, or biocompatible liquid-liquid emulsions or microemulsions; these gas-enriched liquids may advantageously contain ancillary therapeutic agents that are desirable to be delivered in combination with the gas-enriched liquid. In the case of liquid-liquid emulsions or microemulsions (for example perflouorocarbons, or PFC's), a dispersed non-aqueous phase may be incorporated stably into the solution by conventional means in order to enhance gas solubility or incorporate non-aqueous therapeutic agents. Examples of physiologic solutions include ion-balanced salt solutions, such as those which contain calcium, sodium, magnesium, potassium, and mixtures thereof. It will also be appreciated that suitable physiologic solutions may include pH buffers selected from a group consisting of phosphates, bicarbonates, and mixtures thereof. Additionally, the physiologic solution may comprise a physiologically balanced salt solution and an oncotic agent selected from the group consisting of albumen, hydroxyethyl starch, and mixtures thereof. It may also be helpful to provide a physiologic solution including a balanced salt solution and a perfluorocarbon, for example. It will be readily apparent that other equivalent substitutes may be selected, but for brevity they are not specifically enumerated here.

The system of the present invention may be used with any bodily liquid. For example, the system may be used to enrich blood, cerebrospinal fluid, or interstitial liquid. For example, in one embodiment, the bodily liquid is blood and the enclosed area is the coronary vasculature. The enclosed area may be a blood vessel and the surfaces surrounding the enclosed area are walls of the blood vessel.

Preferably, the angle $\alpha$ between the first ends of the capillaries is such that the exit jets from the capillaries, which are laminar jets, collide and form an efficient mixing zone, enabling rapid elimination of concentration gradients and realization of a uniform mixing cup concentration. In one embodiment, the a is between 20° and 150°. In another embodiment, a is between 30° and 120°. In still another embodiment, a is 90°.

In the preferred embodiment, no observable bubbles are formed in the gas-enriched bodily liquid. To help minimize or eliminate the formation of clinically significant bubbles, the blood contact surfaces of the capillaries are exposed to or coated with blood proteins for some brief time interval, usually at least several minutes, before initiating infusion of oxygen-supersaturated liquids. Exposure of the capillary surfaces to proteins is equivalent to providing a wettable surface-active coating, which acts to limit the potential for heterogeneous bubble nucleation from the surface. Similarly, other liquid contact surfaces are exposed to or pre-wetted with liquids and/or hydrophilic agents or coatings, e.g., saline, ethanol and benzalkonium heparin, before use. The liquid contact surfaces also do not include any substance which promotes such bubble formation, e.g., hydrophobic or non-water wettable surfaces that have low surface free energy and high observed contact angles with water, namely Teflon, Teflon-composite liners, silicone oils, etc. Hydrophilic liquid contact surfaces, achieved through judicious material selection or coating methods, are typically useful.

Figure 2A:
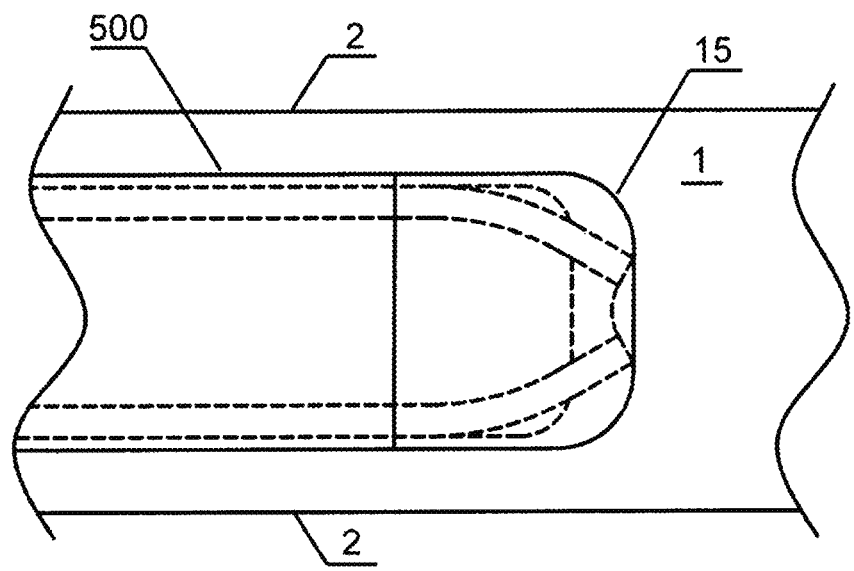
FIGS. 2A and 2B depict the system of the present invention implemented in a catheter tip positioned inside an enclosed area of a body in accordance with another embodiment of the present invention.
Figure 2B:
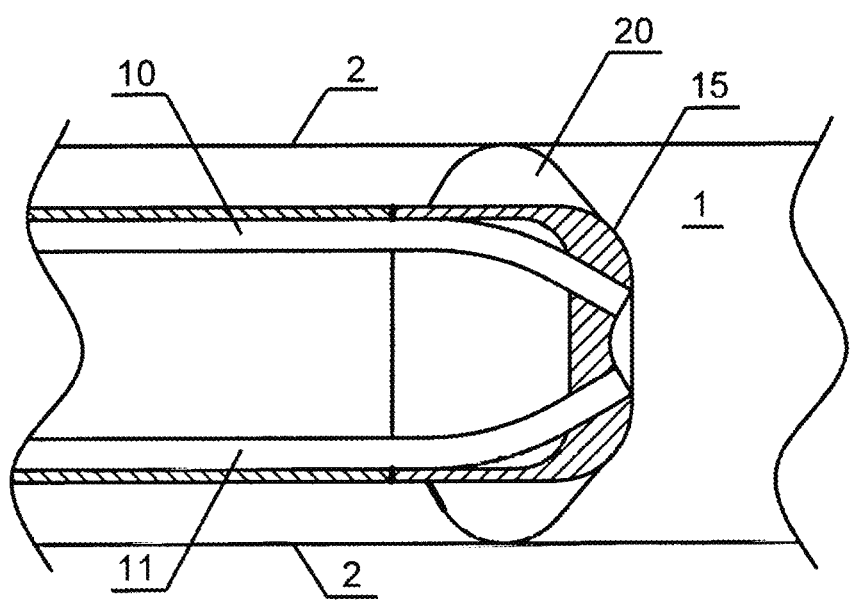

In the case of delivery of gas-enriched liquid to the vasculature, the system of the present invention may be used in conjunction with angiographic or guiding catheters, arterial sheaths, and/or other vascular access devices used in angioplasty and in other interventional cardiovascular procedures. In one embodiment depicted in FIGS. 2A and 2B, the capillaries 10 and 11 are contained within a tip cover 15 of a catheter 500 adapted for positioning within the enclosed area 1 in fluid communication with the bodily liquid. The catheter tip arrangement provides adequate mixing of the gas-enriched liquid with bodily liquid in a manner that produces a gas-enriched bodily liquid without formation of bubbles. As shown in FIG. 2B, the catheter tip cover 15 fixes the positions of two or more capillaries such that their jets collide. The outer surface of the catheter tip cover 15 could be rounded, for example, for atraumatic entry into a conduit such as a blood vessel. A centering feature 20 could be added to improve positioning of the catheter inside the body in a way that prevents close contact between the streams of the gas-enriched liquid with surfaces surrounding the enclosed area. In pipe flow, "close contact" is within the boundary layer near the wall where the velocity v=0, thus it is different from a "contact" which is physically touching the wall]. The centering feature 20 is a mechanical attachment with an outer diameter sized slightly smaller than the internal diameter of a blood vessel (boundary surfaces) 2, but larger than the outer diameter of the catheter to ensure that catheter does not touch the walls of the blood vessel, and that the exit jets from the capillaries do not impinge on the vessel walls. The centering device, for example, could be a fin or wire loop that would have a low profile until the catheter was in position, then could be expanded to center the catheter.

Figure 3A:
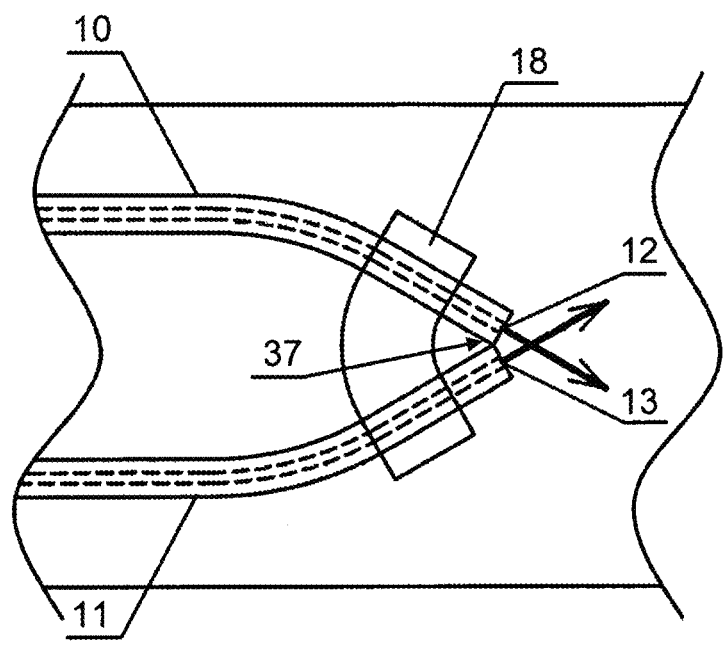
FIGS. 3A and 3B show the system of the present invention comprising two capillaries attached to each other and positioned inside an enclosed area of a body in accordance with another embodiment of the present invention.

The first ends of the capillaries may be connected to each other in such a way that allows the effluent streams of the gas-enriched liquid to collide and convectively mix before exposing the boundary surfaces surrounding the enclosed area to highly supersaturated gas concentrations. Such an arrangement greatly improves lateral stability of the capillaries. For example, in embodiments shown in FIGS. 3A and 3B, a longitude cross-section of each capillary 10 and 11 has a surface facing toward the other capillary and these surfaces are connected at the first ends 12 and 13. In the embodiment shown in FIG. 3A, two separate capillaries are attached to each other by any acceptable method known to those skilled in the art. Such methods include, but are not limited to, chemical adhesion, mechanical attachment as shown using holder 18, and thermal attachment achieved by partially melting capillaries 10 and 11 at the curved internal wall of the capillary 37, pressing them together and then allowing the capillaries to cool.

Figure 3B:
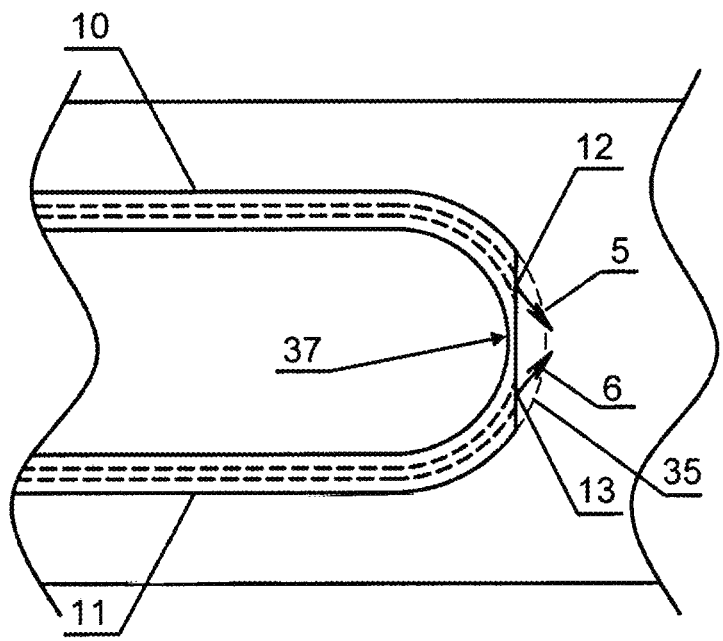

In the embodiment shown in FIG. 3B, a single lumen polymer capillary tube is formed approximately 180° around a round tool (not shown). The form tool and tube are placed in an oven and baked to fix the obtained round shape of the capillary. Then, a curved segment 35 is cut from the apex of the capillary, exposing the inner lumen and forming first ends 12 and 13 from which two streams 5 and 6 of the gas-enriched solution can exit. The curved segment 35 of the capillary is cut in such a way that curved internal wall 37 remains intact.

Figure 4C:
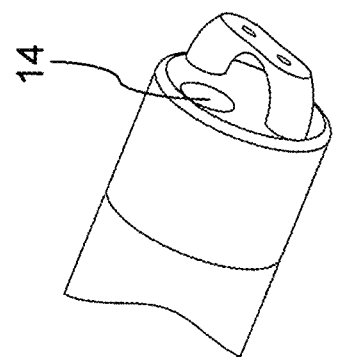
FIGS. 4A, 4B and 4C shows detailed views of various catheter tip configurations.
Figure 4B:
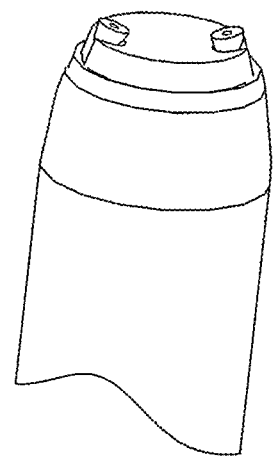
Figure 4A:
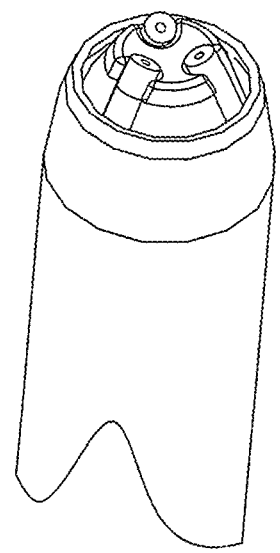

In the embodiments shown in FIG. 4, separate capillaries can be fixed into a tip configuration over a molded or extruded internal form. For clarity, the tip cover 15 (as shown in FIG. 2) is not shown. Each separate glass or polymer capillary tube is inserted into a slot on a tip adapter, then an outer sleeve of shrink-fit tubing (for example, polyether block amide or PEBAX) secures the capillaries to the adapter in the proper alignment for intersecting jets. Two, three, or more capillaries can be aligned in this manner. The catheter tip could provide a passage 14 for a guide wire.

Fluid Delivery Catheter

Figure 5A:
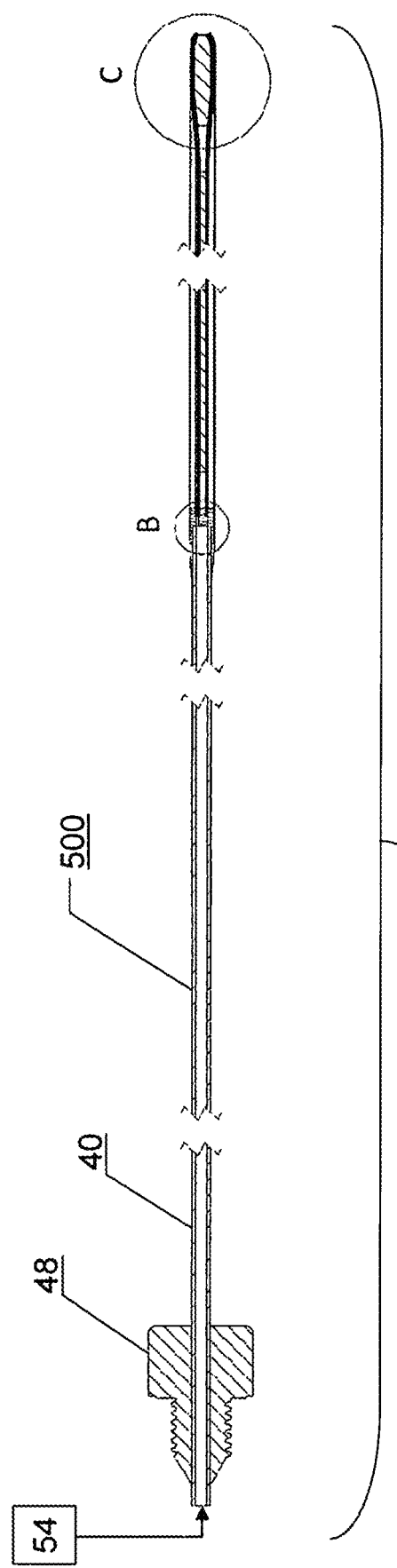
FIGS. 5A, 5B and 5C presents a catheter, including a transition between single lumen of catheter and capillaries in accordance with one embodiment of the present invention.
Figure 5C:
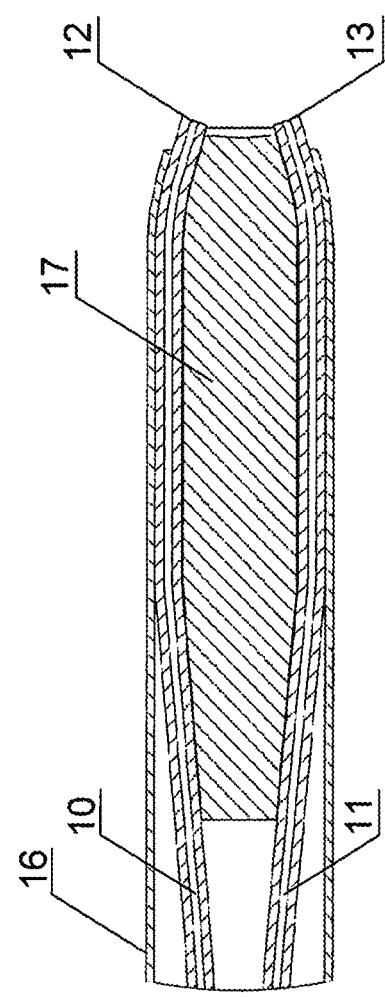
Figure 5B:
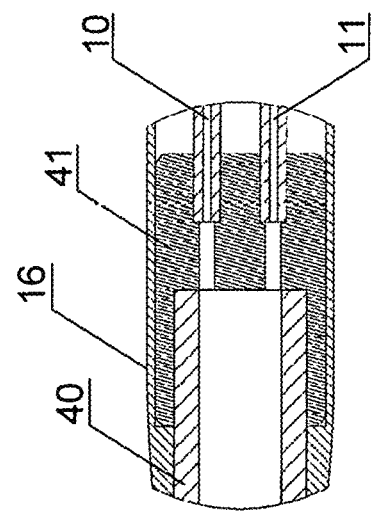

Typically, the fluid delivery catheter 500, as shown in FIGS. 5A, 5B and 5C is sized to fit within a 6 French guide catheter. Materials such as polyethylene, polyetherimide (ULTEM), polyether block amide (PEBAX), or silicone, for example, may be used in the construction of the catheter. The oxygenation device 54 can be connected to catheter 500 by any acceptable means for a high pressure connection. For example in one embodiment shown in FIGS. 5A, 5B and 5C, the catheter has a threaded compression type conical fitting 48 which connects to a port on the oxygenation device 54. Other connections, such as standard luer lock fittings used on medical tubing, are also possible.

This oxygen-enriched saline is delivered from the fluid oxygenation device 54 to catheter 500 via the single lumen tube 40 and to the capillaries 10 and 11 via a transition 41. The catheter 500 is designed to create a relatively low pressure drop from the oxygenation device 54, through single lumen tube 40 and transition 41. Most of the pressure drop in the catheter occurs in capillaries 10 and 11.

In one embodiment, the capillaries in the catheter tip are also enclosed within a tip sleeve 16. Tip sleeve 16 may be attached to transition 41 by any suitable means. Methods of attachment of two elements are known by those skilled in the art and may include chemical adhesion or over molding. A tip cover 15 (not shown for clarity) could be adhesively attached, mechanically attached, or incorporated into the over molded tip sleeve 16. The internal form 17 aligns and supports the capillaries.

Alternatively, catheter 500 can form an integral catheter sleeve (not shown) with internal transition 41 from a single lumen tube 40 to the capillaries 10 and 11. The internal transition from single lumen tube 40 to multiple capillaries 10 and 11, can be achieved in a single, low profile transition 41. This transition would be joined to the capillaries 10 and 11, using chemical adhesives or solvent bonding.

Oxygenation Device (Cartridge)

Figure 6A:
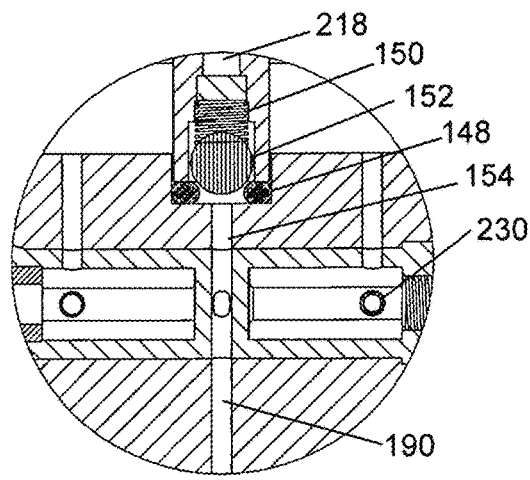
FIGS. 6A, 6B, 6C and 6D presents the system of the present invention comprising a cartridge for providing a gas-enriched liquid to a catheter in accordance with another embodiment of the present invention.
Figure 6B:
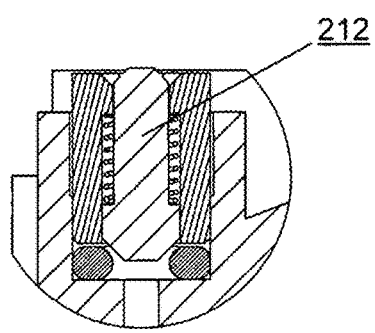
Figure 6C:
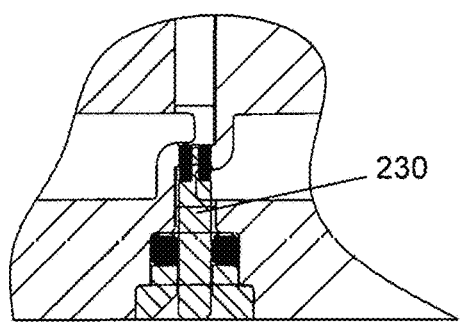
Figure 6D:
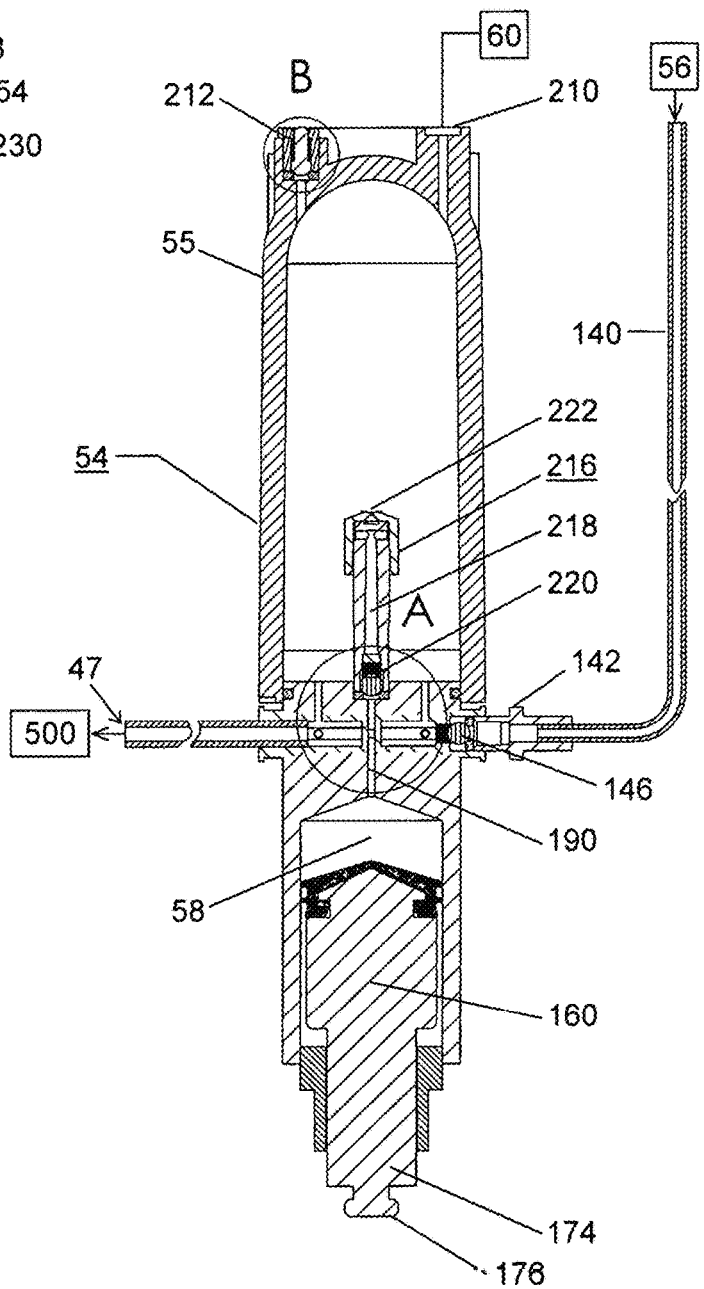

Although, as discussed above, various gas-enriching devices may be suitable for supplying gas-enriched liquid to the capillaries, in one embodiment shown in FIGS. 6A, 6B, 6C and 6D, the system of the present invention may further comprise a cartridge 54 operatively coupled to the fluid delivery catheter 500 through exit port 47 and providing the gas-enriched liquid to the capillaries. The cartridge 54 comprises housing 55 and a gas-enriching device, such as gas-enriching device with an atomization chamber 62. As shown in FIG. 6D, the cartridge 54 further comprises a fluid supply chamber 58. The cartridge 54 is advantageously sterile, removable, and disposable, so that after the procedure on a patient has been completed, it may be removed and replaced with another cartridge 54 for the next patient.

As mentioned previously, the oxygenation device 54 includes two chambers: a fluid supply chamber 58 and an atomization chamber 62. Although various relative positioning of two chambers is possible, in one embodiment, illustrated in FIG. 6D, the chambers are positioned vertically along the same centerline (atomization chamber 62 above the fluid supply chamber 58).

A liquid, such as physiologic liquid (or saline), is delivered from a suitable supply 56, such as an IV bag, to the fluid supply chamber 58 of the cartridge 54 under the control of a system controller (not shown). A suitable gas, such as oxygen, is delivered from a supply 60, such as a tank, to the atomization chamber 62 of the cartridge 54. Although the system of the present invention can operate with any gas, liquid, and bodily liquid, for clarity and simplicity the following description will refer to oxygen, saline, and blood, respectively. The saline from the fluid supply chamber 58 is pumped into the oxygen-pressurized atomization chamber 62 and atomized to create oxygen-enriched saline.

An appropriate delivery device, such as a tube 140, is coupled to a supply of physiologic liquid. In this example, the tube 140 is coupled at one end to an IV bag 56. The other end of the tube 140 is coupled to inlet port 142 of the fluid supply chamber 58. The inlet port 142 forms a fluid passageway that leads to the fluid supply chamber 58 through passageway 190. A check valve 146 is disposed in the inlet port 142 so that fluid may enter the passageway 190 through the inlet port 142, but fluid cannot exit through the inlet port 142.

As illustrated by FIG. 6D, check valve 146 is disposed between a lip in the fluid passageway 190 and the inlet port 142. (This ball-type check valve is similar to the embodiment disclosed in U.S. Pat. No. 6,613,280). Detail of a representative check ball is shown in FIG. 6A. A spring 150 biases a ball 152 into contact with the O-ring seal 148. When fluid moving in the direction of the arrow 154 overcomes the force of the spring 150 and the pressure within the fluid supply chamber 58, the ball 152 is pushed against the spring 150 so that fluid may flow into the fluid supply chamber 58. However, fluid cannot flow in the opposite direction because the ball 152 efficiently seals against the O-ring seal 148.

Referring to FIG. 6D, a piston assembly 160 is disposed at the opposite end of the fluid supply chamber 58. The piston assembly 160 is moveable. To facilitate this movement, a device to be described below is coupled to the free end 174 of the piston assembly 160. Although such coupling may occur in various suitable manners, in this example a key 176 is provided at the free end 174 of the piston assembly 160. The key 176 allows a device to latch onto the piston assembly 160 and move it between the first and second positions.

Referring additionally to FIG. 6D, the fluid supply chamber 58 further includes a second fluid passageway 190. As illustrated by way of a specific example in the present embodiment, the fluid passageway 190 is coupled to an inlet to a valve assembly (not shown) that controls the manner in which fluid from the fluid supply chamber 58 is delivered into the atomization chamber 62.

In operation, the piston assembly 160 within the fluid supply chamber 58 acts as a piston pump. As the piston assembly 160 retracts, fluid is drawn into the chamber 58 from the fluid supply 56. No fluid can be drawn from passageway 190 because valve assembly is closed and a check valve 146 is closed in this direction. As the piston assembly 160 extends, the fluid within the chamber 58 is pressurized, typically to about 670 psi, and expelled from the fluid supply chamber 58 through the fluid passageway 190. The outlet of the fluid supply chamber 58 is coupled to an inlet of the atomization chamber 62 via an appropriate fluid passageway. Further shown in FIG. 6D, a gas, such as oxygen, is delivered under pressure to the atomization chamber 62 via a passageway 210. For example, the oxygen tank 60 may be coupled to the inlet of the passageway 210 to provide the desired oxygen supply. The gas can be vented from the atomization chamber 62 via a vent valve 212. In this embodiment, the vent valve 212 (further shown in detail as FIG. 6B) is controlled by external hardware (cartridge enclosure, not shown) in a manner similar to the embodiment (described in U.S. Pat. No. 6,613,280).

As shown in FIG. 6D, the atomizer 216 includes a central passageway 218 in which a one-way valve 220 is disposed. In this embodiment, the one-way valve 220 is a check valve similar to check valve 146. Accordingly, when the fluid pressure overcomes the force of the spring in the one-way valve 220 and overcomes the pressure of the gas within the atomizer chamber 62, the fluid travels through the central passageway 218 and is expelled from a nozzle 222 at the end of the atomizer 216.

The nozzle 222 forms fluid droplets into which the oxygen within the atomization chamber 62 diffuses as the droplets travel within the atomization chamber 62 shown in FIG. 6D. In this embodiment, the nozzle 222 forms a droplet cone defined by the angle α, which is typically about 20 degrees to about 40 degrees at normal operating pressures, e.g., about 600 psi, within the atomization chamber 62. The nozzle 222 is a simplex-type, swirled pressurized atomizer nozzle including a fluid orifice of about 0.004 inches diameter to 0.005 inches diameter. It should be appreciated that the droplets infused with oxygen fall into a pool at the bottom of the atomizer chamber 62. A more detailed description of the atomizer chamber is provided in U.S. Pat. No. 6,613,280, the relevant content of which is incorporated herein in its entirety by reference.

Since the atomizer 216 will not atomize properly if the level of the pool rises above the level of the nozzle 222, the level of the pool is controlled to ensure that the atomizer 216 continues to function properly. The system monitors a liquid level sensor (not shown) to maintain minimum level in atomization chamber 62. A second (Low) level sensor monitors if level is too low to safely operate, and can stop gas-enriched liquid delivery.

As shown in FIG. 6D, the oxygen is dissolved within the atomized liquid to a much greater extent than liquid delivered to the atomizer chamber 62 in a non-atomized form. Typically, the atomizing chamber operates at a constant pressure from about 100 psi to about 800 psi. Operating the atomizer chamber 62 at any pressure above 100 psi, advantageously promotes finer droplet formation of the physiologic solution from the atomizer 216 and saturation of the gas in the physiologic liquid. In one embodiment, the operating pressure is about 600 psi. The oxygen-enriched liquid formed within the atomizer chamber 62 is delivered to catheter 500 via the catheter exit port 47.

Because it is desirable to control the extent to which the patient's blood is enriched with oxygen, it may be desirable to dilute the oxygen-supersaturated liquid to reduce its oxygen content. Any suitable valve arrangement and type of valve may be used. For example, in one embodiment, the valves are needle valves that are normally biased in the closed position. Details of these valves are described in U.S. Pat. No. 6,613,280, the relevant content of which is incorporated herein by reference. A representative needle valve 230 is shown in FIG. 6C. In one embodiment, a valve assembly is provided and is disposed in the housing. The valve assembly has valves to control flow of the fluid between the fluid supply device and the enrichment device and controls flow of the gas-enriched liquid between the enrichment device and the capillaries.

Although an atomizing chamber provides a convenient mechanism for diffusing relatively large amounts of gas into a liquid in a relatively short period of time, it is not the only way of dissolving gas within a liquid. Indeed, other devices, such as membrane oxygenators, gas spargers, bubblers, and thin film oxygenation devices, may be used to perform this function as well. Furthermore, although a piston pump similarly provides a compact and efficient method of pressurizing liquid prior to sending it to an oxygenator, such as the atomizer, other types of pumps or methods of pressurization may be used as well. Therefore, although a piston pump and atomizer are utilized in the exemplary embodiment of the system of the present invention, other devices may perform these functions.

With these generalities in mind, as shown in FIG. 6D, the oxygenation device 54 disclosed herein offers several advantages that make it particularly attractive for use within a medical environment. First, the oxygenation device 54 may be advantageously made from a clear plastic, such as polycarbonate which can be molded to provide a high strength, low cost device. Second, the oxygenation device 54 may be implemented in a relatively compact format, with an exemplary specimen measuring approximately 12 cm in height and 3 cm in diameter. Third, the oxygenation device 54 combines the preparation of the oxygen-enriched liquid, along with the mixing of the oxygen-enriched liquid with the blood, into a unitary device utilizing only three connections: (1) liquid supply, (2) oxygen supply, and (3) catheter connection port. The user connects the fluid supply (IV bag) and the fluid delivery catheter to the cartridge. The other connections are within the oxygenation device 54 itself, or are incorporated into the cartridge enclosure, and they require no additional connection from the user after loading the cartridge. Also, all of the valves used to operate the oxygenation device 54 are integrated within its unitary structure. Thus, the valves and their associated fluid passageways are protected against external contamination, and users are protected against any contamination that may arise from the use of the various fluids as well. As a result, the oxygenation device 54 is a relatively contamination-free cartridge that may be used during a surgical procedure on a patient, and then removed and replaced prior to performing a surgical procedure on the next patient.

Finally, the oxygenation device 54 allows to create oxygen-enriched saline and deliver it directly to the patient's coronary vasculature through the fluid delivery catheter where it adequately mixes with the blood without creating bubbles.

Hardware Enclosure (Cartridge)

Although, as discussed above, various gas-enriching devices may be suitable for supplying gas-enriched liquid to the capillaries, in one embodiment shown in FIG. 6D, the oxygenation device (cartridge) 54 of the present invention would be operated by a hardware component (not shown) that controls the operation of the cartridge. Specifically, this hardware component would contain the cartridge, operate externally controlled needle or vent valves, operate the piston, operate the gas supply, and monitor conditions within the cartridge (liquid levels, pressures, flow rate). This hardware component would have a controller to perform these functions, and a display to inform the user and receive user input. An embodiment capable of these functions is described in U.S. Pat. No. 6,613,280, and the relevant content of which is incorporated herein in its entirety by reference, Capillary Construction Methods In another aspect, the present invention provides a method of assembling a system for enriching a flowing liquid with a dissolved gas inside a conduit. The method comprises: (a) providing two capillaries for delivery of a gas-enriched liquid, each with a first end and a second end; (b) positioning the first ends of the capillaries to form an intersecting angle with respect to the effluent streams such that these streams of gas-enriched liquid collide with each other upon exit from the first ends of the capillaries, effecting localized convective mixing within the larger liquid conduit before these gas-enriched streams are able to come into close contact with the boundary surfaces of the conduit; and (c) operatively connecting second ends of the capillaries to a source of the gas-enriched liquid.

In one embodiment shown in FIG. 7, the step (a) of the method comprises: (a1) providing a polymer capillary tube 400 with a single lumen 401; (a2) wrapping the tube 400 around a curved tool 402 with a known radius R to form a capillary of a modified shape having a curved segment 403; and (a3) cutting and removing a part of the curved segment to form two capillaries with exposed lumen.

In one embodiment, the step (a2) further comprises a step of fixing the modified shape of the capillary. On one embodiment, discussed in more detail in Examples that follow, the fixing is carried out by placing the form tool and capillary in an oven and baked them at approximately 350° F. for about 60 minutes to stress relieve the capillary.

For example, in one embodiment, a single lumen polymer capillary tube, made from polyetherimide, is formed approximately 180° around a tool with a known radius, of 0.100 inch or smaller. The form tool and tube are placed in an oven and baked at approximately 350° F. to stress relieve the capillary. Baking also allows the capillary to retain its shape during the bonding process at assembly. The formed capillary is placed into a trimming fixture, and a circular segment is cut from the apex of the capillary, exposing the inner lumen. The radius of the capillary and the depth of the trimmed segment control the angle of the exit jet streams; this angle is preferably 90° included. As a final step, the overall length of the capillary is trimmed to the final size.

Figure 7A:
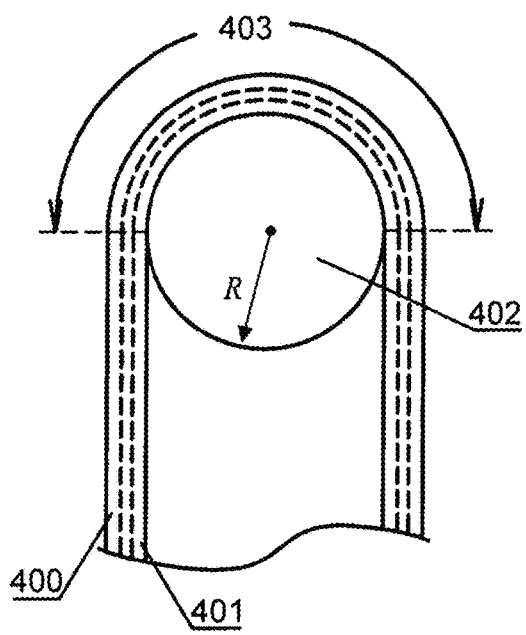
FIGS. 7A, 7B, 7C and 7D shows steps of making catheter tip configurations with capillaries in accordance with some embodiments of the present invention.
Figure 7B:
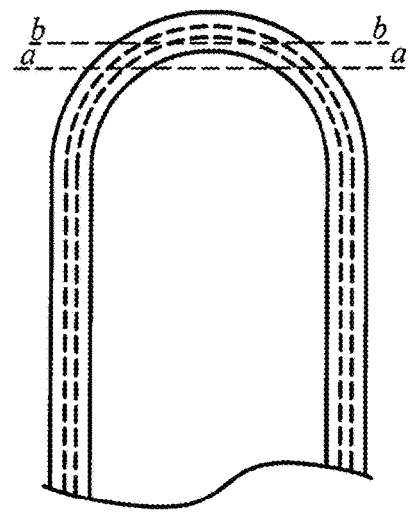
Figure 7C:
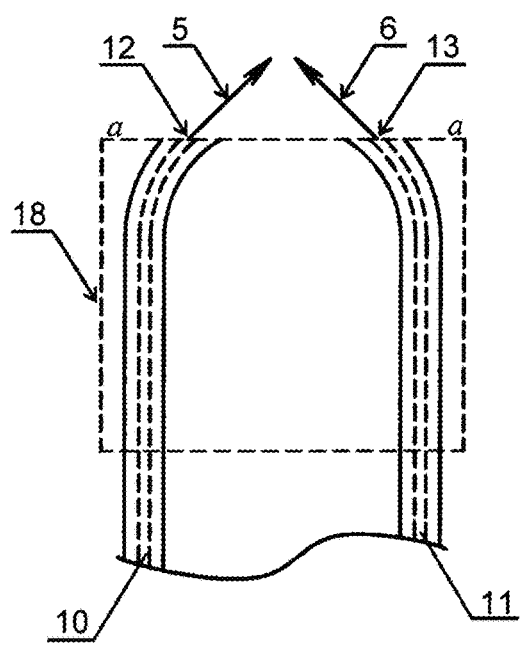
Figure 7D:
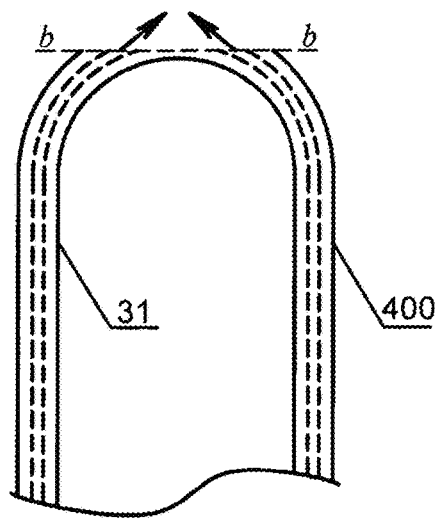

As shown in FIGS. 7B and 7C, the curved segment 403 may be cut as shown by line a-a to form two curved capillaries 10 and 11 with curved first ends 12 and 13 from which streams 5 and 6 of the gas-enriched liquid exit. The capillary tube 400 may be attached to or contained by holder 18 after forming but prior to cutting. Alternatively, as shown in FIGS. 7B and 7D, the curved segment 403 may be cut as shown by line b-b in such a way that the curved internal wall 37 of a longitudal cross-section of the capillary remains intact and a capillary 400 with two exits for gas-enriched liquid is formed. The radius of the curved tool 402 and the depth of the trimmed segment control the angle at which the streams 5 and 6 of the gas-enriched liquid exit. In one embodiment, the angle is between 20° and 150°, preferably between 30° and 120°. In one embodiment, the angle is about 90°. In a further embodiment, the radius of the curved tool is less than 0.10 inch.

The obtained capillaries 10 and 11 each having a single lumen or a single capillary 400 may be positioned inside a catheter as shown in FIG. 2. The catheter is adapted to be inserted into the enclosed area inside the body in communication with a bodily liquid. For example, in one embodiment, the capillary (or capillaries) is/are assembled into the distal tip of an angioplasty device. An oxygen-enriched liquid is introduced into the proximal ends of the capillary tube. Jet streams of the oxygen-enriched liquid exit from the apex of the capillary, at opposing 45° angles (90° inc.) and collide just distal to the tip. The resulting impingement of the two exit jets rapidly mixes the oxygen-enriched liquid with the surrounding blood, eliminating large concentration gradients in favor of the mixing cup concentration and elevating the blood $pO_2$ to hyperbaric levels.

In another aspect, the present invention provides a method of enriching a flowing liquid with a dissolved gas inside a conduit. The method comprises: (a) providing two capillaries for delivery of a gas-enriched liquid, the capillaries having first and second ends, wherein the first ends of the capillaries are positioned to form an intersecting angle with respect to the effluent streams such that these streams of gas-enriched liquid collide with each other upon exit from the first ends of the capillaries, effecting localized convective mixing within the larger liquid conduit before these gas-enriched streams are able to come into close contact with the boundary surfaces of the conduit; and (b) delivering the gas-enriched liquid through the capillaries to form a gas-enriched bodily liquid.

In one embodiment, the capillaries are contained within a tip of a catheter adapted for positioning within the body in a communication with the bodily liquid. The catheter may further comprises an aligning device. Then, the positioning step (b) of the above method further comprises a step of using the aligning device to position the catheter inside the body in a way that prevents a contact between the streams of the gas-enriched liquid with the surfaces surrounding the enclosed area prior to the mixing of the gas-enriched liquid with the bodily liquid.

The present invention may be embodied in other specific forms without departing from its essential characteristics. The described embodiments are to be considered in all respects only as illustrative and not as restrictive. The scope of the invention is, therefore, indicated by the appended claims rather than by the foregoing description. All changes which come within the meaning and range of the equivalence of the claims are to be embraced within their scope.

What is claimed is:

1. A catheter, comprising:
   a catheter tube;
   a first capillary, wherein at least a portion of the first capillary is positioned in the catheter tube; and
   a second capillary, wherein at least a portion of the second capillary is positioned in the catheter tube;
   wherein the first capillary is configured to deliver a first stream of a gas-enriched liquid;
   wherein the second capillary is configured to deliver a second stream of gas-enriched liquid;
   wherein the first capillary and the second capillary are configured such that the first stream, upon exit from the first capillary, collides with the second stream, upon exit from the second capillary, effecting localized convective mixing within a conduit before either the first stream or the second stream come into contact with the conduit.

2. The catheter of claim 1, wherein the first capillary is configured to cause the first stream to have laminar flow, and wherein the second capillary is configured to cause the second stream to have laminar flow.

3. The catheter of claim 1, wherein no observable bubbles are formed in the gas-enriched flowing liquid where the localized convective mixing is configured to occur.

4. The catheter of claim 1, wherein the gas-enriched liquid has a hyperbaric dissolved oxygen concentration.

5. The catheter of claim 1, wherein the first capillary, the second capillary, or each of the first capillary and the second capillary has a single lumen with a diameter between about 25 microns to about 300 microns.

6. The catheter of claim 1, wherein the conduit includes a blood vessel and wherein the localized convective mixing is effected before the first stream and the second stream are configured to collide with walls of the blood vessel.

7. The catheter of claim 1, wherein the catheter tube comprises a passage configured to receive a guide wire.

8. The catheter of claim 1, wherein the first capillary and the second capillary each have an internal wall and an external wall to form respective lumens, wherein a first internal wall of the first capillary is connected to a second internal wall of the second capillary.

9. The catheter of claim 1, wherein the first capillary and the second capillary each have an internal wall and an external wall to form respective lumens, and wherein walls of the first capillary are not connected to walls of the second capillary.

10. The catheter of claim 1 further comprising a cartridge that is operatively coupled to the first capillary and the second capillary for providing the gas-enriched liquid.

11. The catheter of claim 10, wherein the cartridge comprises a housing and a gas-enrichment device disposed in the housing to form the gas-enriched liquid.

12. The catheter of claim 11, wherein the gas-enrichment device comprises a gas-pressurized atomizing chamber that is adapted to receive gas into an atomizer disposed within the atomizing chamber, wherein the atomizer is adapted to receive a liquid and to atomize the liquid upon delivery into the gas-pressurized atomizing chamber to form the gas-enriched liquid.

13. The catheter of claim 12, wherein the cartridge comprises a liquid supply device disposed in the housing to supply the liquid to the gas-enrichment device.

14. The catheter of claim 13, wherein the liquid supply device comprises:
a liquid supply chamber having a liquid flow inlet and a liquid flow outlet; and
a pump disposed within the liquid supply chamber, the pump adapted to
draw the liquid into the liquid supply chamber through the liquid flow inlet in the liquid supply chamber, and
deliver the liquid to the gas-enrichment device through the liquid outlet in the liquid supply chamber.

15. The catheter of claim 13, wherein the cartridge comprises a valve assembly disposed in the housing, the valve assembly having valves to control flow between the liquid supply device and the gas-enrichment device and to control flow of the gas-enriched liquid between the gas-enrichment device and the first capillary and the second capillary.

16. The catheter of claim 13, wherein the liquid supply device and the atomizing chamber are positioned coaxially.

17. The catheter of claim 1, further comprising a centering feature configured to prevent the catheter tube from touching walls of the conduit and prevent the first stream and the second stream from contacting the conduit prior to the first stream mixing with the second stream.

\* \* \* \* \*